United States Patent [19]

Timmermans et al.

[11] Patent Number: 5,076,107
[45] Date of Patent: Dec. 31, 1991

[54] APPARATUS AND METHOD FOR RESULTANT-WEIGHT MEASURING SYSTEM

[75] Inventors: Jacques Timmermans, Brussels; André J. Moës, Ans, both of Belgium

[73] Assignee: G. D. Searle & Co., Chicago, Ill.

[21] Appl. No.: 289,841

[22] Filed: Dec. 27, 1988

[51] Int. Cl.$^5$ .............................................. G01N 5/04
[52] U.S. Cl. ........................................ 73/866; 73/437; 73/865; 177/50
[58] Field of Search .................... 73/580, 437, 432.1, 73/865.8, 866, 866.2, 865; 177/187, 210 FP, 50

[56] References Cited

U.S. PATENT DOCUMENTS

| | | | |
|---|---|---|---|
| 3,791,221 | 2/1974 | Kirschner et al. | 73/866 |
| 3,896,792 | 7/1975 | Vail et al. | 73/23 X |
| 3,901,232 | 8/1975 | Michaels et al. | |
| 4,055,178 | 10/1977 | Harrigan. | |
| 4,126,672 | 11/1978 | Sheth et al. | 424/22 |
| 4,167,558 | 9/1979 | Sheth et al. | 424/22 |
| 4,247,298 | 1/1981 | Rippie | 73/866 |
| 4,335,438 | 6/1982 | Smolen | 73/866 |
| 4,593,563 | 6/1986 | Laine et al. | 73/865.8 |

FOREIGN PATENT DOCUMENTS

2163648 3/1986 United Kingdom .

Primary Examiner—Tom Noland
Attorney, Agent, or Firm—J. Timothy Keane; Paul D. Matukaitis

[57] ABSTRACT

Apparatus and method are described for measuring and recording as a function of time the resultant-weight of a test object immersed in a fluid medium. The apparatus and method are particularly suitable for determining a change in a chemical and/or physical property of a material exposed to a fluid, and for measurements such as of the floating forces produced by buoyant pharmaceutical dosage forms. An electronic toploader balance, with a weight-transmitter device connected to an electromagnetic measuring module of the balance, is positioned above a container so that the lower end of the weight-transmitter device extends into a solvent within the container. The weight transmitter device performs the double function of holding the test object submerged in the solvent and of transmitting to the balance the reacting force, that is the resultant-weight of the test object.

3 Claims, 7 Drawing Sheets

APPARATUS AND METHOD FOR RESULTANT-WEIGHT MEASURING SYSTEM

FIELD OF THE INVENTION

This invention relates to systems for measuring the resultant-force acting on test objects which are partially or wholly immersed in a fluid medium. Such systems are useful generally to determine the immersed weight of any solid gelatious, pasty, oily or non-miscible material exposed to any solvent. In pharmaceutical applications, such systems are particularly useful to measure the resultant-weight of a buoyant or non-buoyant pharmaceutical dosage material, wholly or partially immersed in a solvent, as well as changes in a chemical and/or physical property of the material as a function of time as the pharmaceutical dosage material dissolves in or interacts with the solvent.

BACKGROUND OF THE INVENTION

Sustained and/or controlled release formulations provide convenient and efficacious methods of administering drugs to animals and humans. There are many advantages to the patient and clinician in extending the gastrointestinal transit time of orally administered controlled release formulations. Attempts have been made to prolong the residence time of sustained and/or controlled release formulations in the stomach by use of dosage materials in a buoyant form.

In such orally-administered sustained and/or controlled release preparations, the non-disintegrating dosage form preferably remains buoyant and freely floating in the gastric fluid for an extended period of time during which substantially all of the medicament contained therein is released into the stomach contents for absorption. For example, U.S. Pat. No. 3,901,232 to Michaels et al. and U.S. Pat. No. 4,055,178 to Harrigan describe the use of such dosage forms equipped with an inflatable chamber. U.S. Pat. No. 3,896,792 to Veil et al describes several coating techniques ensuring the buoyancy of a dosage form. U.S. Pat. No. 4,126,672 and U.S. Pat. No. 4,167,558 to Sheth et al. describe the formulation of hydrodynamically balanced systems, either capsules or tablets, having a bulk density less than one in contact with gastric fluid and remaining buoyant in the stomach.

Systems capable of measuring in vitro the floating force produced by a buoyant dosage form provide useful information as to certain critical characteristics of the products, which information aids in design, development and manufacturing of efficacious controlled release pharmaceutical products. For example, the time during which a capsule or a tablet remains buoyant in the stomach may determine, or at least have a significant effect upon, the amount of active ingredients absorbed and the rate at which the active ingredients will enter the bloodstream. Thus, the residence time of a buoyant dosage form in the stomach can be critical for those classes of active ingredients that are absorbed primarily from the stomach and are not suited to absorption during passage through the intestinal tract due to their physiochemical properties and/or favorable sites of absorption. There are also medicaments, e.g. antacids, which are intended to act in the stomach and lose beneficial properties when such medicaments pass too early into the intestinal tract. Hence, proper control of such residence-time floating duration in the stomach is important in both the design and the manufacturing of buoyant dosage forms.

As a dosage form releases a medicament contained therein, the bulk density and/or weight does not remain constant because during immersion such release is often accompanied by a modification of the weight and/or the volume of the material. Different dosage forms having the same floating duration may exhibit different floating characteristics in time. For example, buoyancy may range from high floating forces to low values close to sinking conditions and, in this last case, be more easily emptied from the stomach of the user. Determination of the floating force that will be developed by a dosage form during its buoyancy period is primarily an empirical exercise inasmuch as there are many intrinsic and extrinsic phenomena which modify the weight and/or the volume of the dosage form. Measurement of resultant weight when immersed as a function of time discloses the real floating characteristics of the product.

Important characteristics other than buoyancy may also be determined by measurement of resultant weight of an immersed material. For example, measurements using such systems provide data as to the melting of a fatty base suppository, the permeability of a film coating, the dissolution of an excipient, the solvation of a material, the erosion or the disintegration of a mass. Determination of such characteristics for a floating or a non-floating pharmaceutical dosage material by resultant-weight measurement, such as provided by the apparatus and method of the invention, enable also establishment of standard physical and/or chemical constants for a test material. Systems for determining such characteristics of a pharmaceutical dosage form may be classified generally as an "active" system, i.e., a system inducing dynamically a measurement and being often a destructive testing system, or as a "passive", i.e., a static measuring system operating in a non-destructive manner. An example of an active system is described in the publication of Washington et. al., Proceedings of the 45th Congress of the F.I.P., Montreal 1985, which shows an apparatus for applying an upwardly-directed pulling force to determine the point of breaking strength of a raft-forming antacid preparation immersed in a solvent. Another example of active system is provided by U.K. Patent No. 2,163,648 of Nippon Shinyaku which mentions a device for measuring the force required to make a floating dosage form sink.

It will be apparent to those skilled in the art of pharmaceutical tests and determinations, upon reading the hereinafter detailed description of the invention, that the present apparatus and method, for effecting resultant-weight measurements of a test object in an immersed condition within a fluid medium, is a "passive" measuring system, with regard to the previous discussion, and therefore differ from the hereabove exemplified "active" systems.

In addition and although the concept of weighing an immersed test material is known, no fully satisfactory "passive" measuring system of a continuous operating nature has been up to now described or proposed in the pharmaceutical technology literature or elsewhere for effecting resultant-weight measurements of various buoyant and non-buoyant pharmaceutical dosage materials, wholly or partially immersed in a solvent, or for determining a change, as a function of time, in a chemical and/or physical property of the material suspended in a fluid medium by measuring a change in a vertical force, acting on said material, under controlled and repeatable conditions.

DESCRIPTION OF THE INVENTION

A system for determining a change in a chemical and/or physical property of a test object which is partially or completely immersed in a fluid medium is provided by apparatus and a method for effecting measurements as a function of time of the resultant-weight of an immersed test object. "Resultant-weight" means the net weight determined by measuring the total force acting vertically on the immersed object which results from the gravity force and the buoyant force. The apparatus comprises means for securing a test object partially or totally immersed within a fluid medium. The apparatus further comprises means for detecting the magnitude of the resultant force acting on the test object, also called herein the "force detecting means". The apparatus further comprises means for transmitting the resultant force, acting on the test object, from said test object securing means to said force detecting means. Such force transmitting means is also called herein the the "weight transmitting means", or the "weight transmitter device". The resultant force transmitted through the buoyant force transmitting means may be positive or negative depending upon whether the test object has a density, respectively, less than the solvent or greater than the solvent in which the test object is immersed. The net force transmitted to the force transmitting means is the resultant-weight of the test object.

The force detecting means includes a measuring module which is preferably an electromagnetic measuring module of a conventional electronic balance chosen for its readability and sensitivity characteristics with respect to the measurements needed or the nature of the material of the test object. The measuring module is accessible preferably underneath the balance in order to connect thereon suitable weight transmitting means provided by a device for transmitting vertically the resultant-weight. Connecting means between the electromagnetic measuring module and the weight transmitter device are provided in a manner to ensure that all vertical displacements of the connected weight transmitter device, due to the application of a vertical force on it, are detected by the measuring module with the same readability, accuracy, sensitivity and reproducibility characteristics as when an identical vertical force is applied on the pan of the balance.

The balance is preferably equipped with data output interface means for connecting to, and delivering a signal automatically to, a display screen showing digital information corresponding to the measurements, or to suitable data recording means such as a digital-analog converter and a paper recorder, or to a computerized system. Assembly of measuring means and recording means is realized preferably in a manner to ensure sustained data collection of kinetic measurements and continuous operation of the apparatus without needing the intervention of an operator after exposure of the test object to the fluid medium and throughout the entire measuring procedure.

Means are provided to compensate for loss of solvent by evaporation and the consequent liquid level lowering in the main vessel holding the solvent. Such level lowering is continuously compensated by suitable means, such as an automatic liquid compensating system. Evaporation has, therefore, no significant effect on the stability and reproducibility of measurements. Preferably, suitable shock absorbing means and/or damping devices are provided between the measuring module and those components of the system which tend to produce continuous or erratic vibrations or movements. The stability of measurements as a function of time is indicated by a linear resultant-weight base-line record, in absence of other forces than those produced by the solvent on the immersed portion of the weight transmitter device. For example, linearity deviations of a maximum $\pm 2$ mg would be expected with the apparatus of the invention. Also, the system should provide resultant-weight drifts not more than $\pm 2$ mg from the base-line throughout the entire measuring procedure.

The system also includes means for controlling or attenuating any intrinsic or extrinsic systematic and/or aleatory interfering phenomena that may occur during the entire measuring procedure which may affect the quality of measurements, or the original readability, accuracy, sensitivity and stability of the measuring module. Examples of phenomena of intrinsic origin are magnetization of the measuring module, temperature increase inside the balance, solvent evaporation, dissolved air in solvent, bubbles trapped by the weight transmitter device and surface tension variation in the solvent. Examples of phenomena of extrinsic origin are ambient temperature variation, drafts and over-or-under pressure caused by room ventilation.

The weight transmitter device typically comprises an upper portion in contact with the measuring module of the balance, a middle or intermediate portion, and a lower portion which terminates within the solvent and holds the test material below the liquid surface. The weight transmitter device upper portion is rigidly connected on one end to the measuring module of the balance and on the opposing end to the intermediate portion of the weight transmitter device. Preferably the upper portion is made of a rigid material, such as Teflon plastic, which is also non-magnetizable, non-conducting of current and non-absorbing of humidity. The weight transmitter device intermediate portion is rigidly connected in a vertical orientation to the upper and lower portions of the weight transmitter device. Preferably, the intermediate portion is in the configuration of a cylindrical rigid shaft and is composed of a material which is non-absorbing of humidity and has a low thermal dilatation coefficient such as stainless steel. The weight transmitter device lower portion, also designated as a "holder extremity", is rigidly connected on one end above the liquid level to the intermediate portion while its opposite end is immersed in the solvent. The lower portion is easily replaceable with holders of various configurations depending upon the dimensions, shape and nature of the test material, the characteristics of the test solvent and the kind of working procedure, such as, for example, whether the test material is to be fully or partially immersed. Preferably, the lower portion is unitary in construction and arched to a small diameter at the air-solvent interface and is fabricated of a rigid material which is non-absorbing of humidity, non-porous, appropriate to the solvent, has a low thermal dilatation coefficient and has no significant physical and/or chemical interactions with either the solvent and/or the test material. An example of a suitable material for fabrication of the lower portion is stainless-steel coated with Teflon plastic.

The holder extremity holds the test material to maintain it at a constant immersion depth below the liquid surface throughout the entire measuring procedure for a variety of test materials, such as floating/ non-floating single-unit or multiple-unit dosage forms and perforable/non-perforable materials under a variety of test conditions, various solvents and immersion depths. The weight transmitter device holder extremity is adapted to the test material such that the holder extremity does not modify significantly the characteristic behavior of the test material in the solvent. Also, it is preferred that the test material may be visually observed throughout the entire measuring procedure.

Materials to be tested, may be, test objects made of a solid, gelatinous, pasty, oily or non-miscible mass and may be in the form of tablets, capsules, pellets, suppositories, implants and similar dosage forms. Test objects may also be unitary in composition or in the form of a composite material including various types of masses, excipients or dosage forms.

Properties or characteristics to be determined for floating and non-floating immersed materials, as a function of time, include absorption, diffusion, disintegration, dissolution, erosion, melting, gas generation, swelling, solvation and similar characteristics. Determination of such characteristics by resultant-weight measurements, provided by the apparatus and method of the invention, enable establishment of standard chemical and/or physical constants for a test material, such as floating duration, melting time, dissolution rate and the like, for comparison against design criteria and manufacturing specifications.

Also included within the system are means for continuously adjusting various experimental parameters and means for modifying such parameters by programming variations or adjustments of the parameters as a function of time throughout the entire measuring procedure, such as solvent pH variations and temperature gradients The test material can be evaluated at various stages of its development, e.g., in research to delineate the phenomena affecting the buoyancy of floating dosage forms, to determine the factors influencing melting kinetics of fatty base suppositories, in development for determining formulation drug delivery characteristics and for predicting in vivo behavior from in vitro tests, and in manufacturing and quality control to achieve uniform product profiles for the formulated products. Other objects and purposes of the present invention will be apparent to persons acquainted with measuring process of this general type upon reading the following specifications and inspecting the accompanying drawings.

DETAILED DESCRIPTION

An apparatus and a method for measuring and recording as a function of time the resultant-weight of an immersed material are now described in more detail.

The specific embodiment of the apparatus here exemplified in the context of pharmaceutical tests and determinations has been chosen for illustrative purposes only and it will be apparent that this embodiment may be freely adapted to other context of resultant-weight measurements and that the invention is applicable in a wide variety of other possible uses both within the pharmaceutical industry and elsewhere.

A container, for holding a suitable solvent, is typically supported in a temperature-controlled bath. An electronic toploader balance, with a weight-transmitter device connected to the bottom of the balance pan of an electromagnetic measuring module, is positioned above the container so that the lower extremity of the weight transmitter device extends into the solvent. The device performs the double function of holding the solid material totally or partially submerged within the solvent, and of transmitting a reacting force to the measuring module of the balance.

A key purpose of the invention is measuring as a function of time the resultant-weight of floating and non-floating pharmaceutical materials, particularly capsules, tablets, pellets, implants and suppositories. The buoyant force exerted by a homogeneous fluid of density, df, on an immersed object of area S perpendicular to its surface, can be considered as the sum of the downward force FB, acting on the top face of the object at depth hB where the pressure is pB, and the opposite upward force FA, acting on the bottom face of the object at depth hA where the pressure is equal to pA.

This buoyant force $F_{buoy}$ has the magnitude:

$$F_{buoy} = FA - FB = pA\ S - pB\ S = df\ g\ hA\ S - df\ g\ hB\ S. \quad (1)$$

Due to fluid pressure increase with depth, $F_{buoy}$ is always positive and directed vertically upward. All other forces exerted by the incompressible fluid at rest can be similarly paired in opposite directions and the resultant horizontal force is zero. By noting that the depth difference is equal to the object height h and that S h is the volume V of the object, the buoyancy force can be written:

$$F_{buoy} = df\ g\ S\ (hA - hB) = df\ g\ V \quad (2)$$

The total force F acting on an immersed object, is obtained by adding the gravity force $F_{grav}$ directed downwards, i.e., the object weight, to the buoyant force. The magnitude and direction of this total force is given by:

$$F = F_{buoy} - F_{grav} = df\ g\ V - ds\ g\ V = (df - ds)\ g\ V \quad (3)$$

When the density ds of the immersed material is lower than the fluid density, the total force F is positive, directed upwards, and after rising to the surface the material floats with only part of its volume submerged. Since the resultant force is zero at equilibrium when the object floats, the magnitude of force F can only be known precisely by maintaining this floating object artificially below the surface of the fluid and measuring the equal reacting upward force transmitted. Identical argumentation applies to a non-floating object having a density ds higher than the fluid density, and an equal reacting downward force is then transmitted when maintaining the object suspended within the fluid. According to the action-reaction principle and the theorem of energy conservation, the force F has the same magnitude as the force needed to maintain the object totally submerged.

In the case of the invention, the weight transmitter device performs the double function of maintaining the solid material submerged in the solvent and of transmitting the reacting force to the electromagnetic measuring module of an electronic balance. Since the force F is transmitted to a balance, the value measured by the apparatus is called the resultant-weight of the test object (its weight diminished by the buoyancy force) and is expressed in weight units. The resultant-weight has a magnitude and direction equal to the total force F noted in equation 3. From equation 3, it is apparent that the resultant-weight of an immersed object is independent of its shape, the material it is made of, the immersion depth and the atmospheric pressure.

Figure 1:
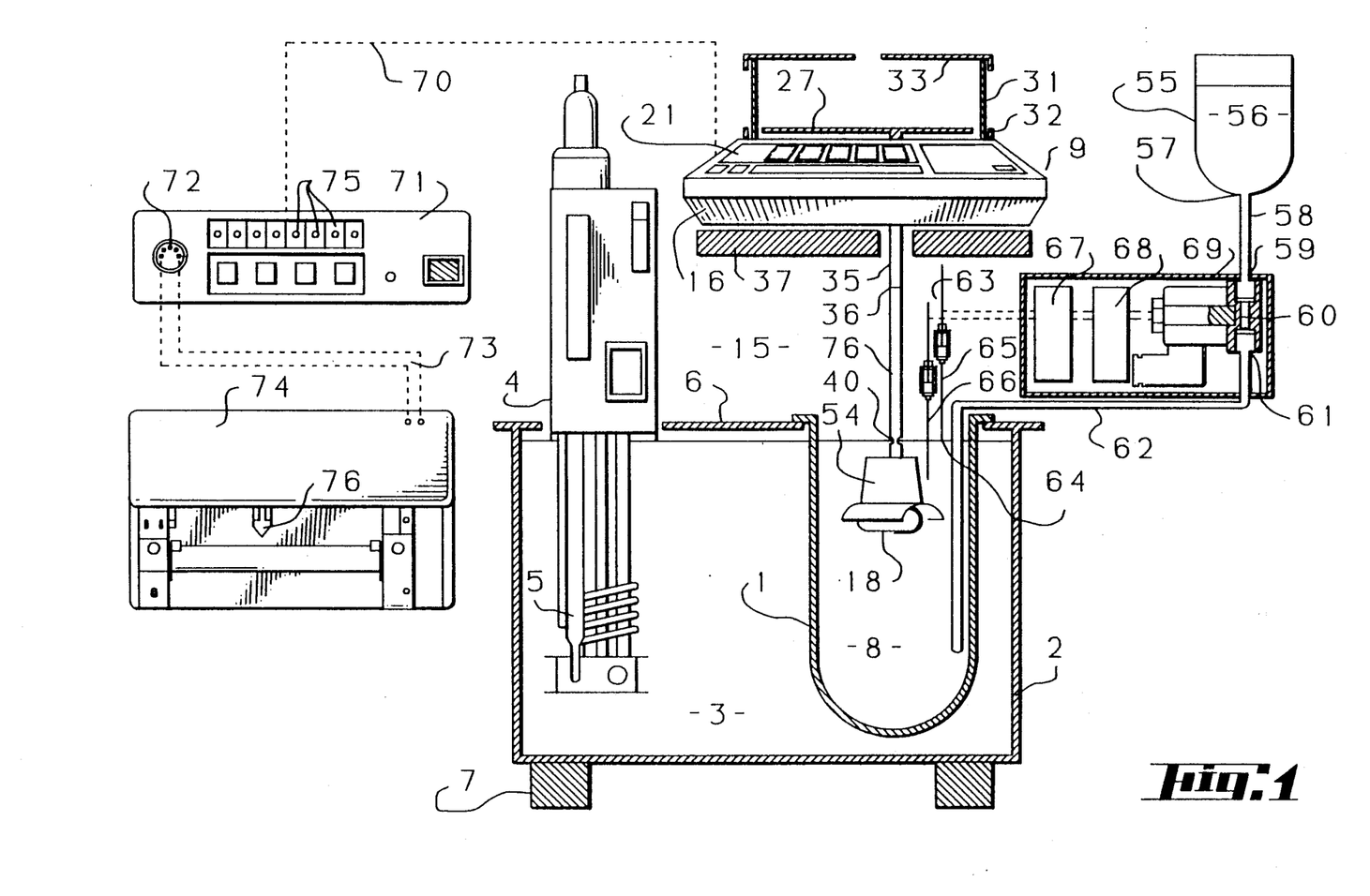
FIG. 1 is a schematic view of the apparatus in full assembly.

In FIG. 1 there is shown a container (1) made of a transparent inert material such as glass and having the dimensions of the USP XX dissolution vessel, i.e., a cylindrical vessel with a spherical bottom, 16.0 to 17.5 cm high, having an inside diameter of 10.0 to 10.5 cm and having its sides flanged near the top. Container (1) may, of course, be constructed of other materials or have dimensions as appropriate to the solvent to be contained and/or the material to be immersed therein. Container (1) is immersed in a suitable water bath (2) of any convenient size that permits controlling the temperature of the solvent within the container (1) at the desired temperature, either above or below the room temperature according to the requirements of the procedure being carried out, and that permits keeping the bath fluid (3) in constant, smooth motion.

Temperature requirements for pharmaceutical dosage forms, i.e., 37.0±0.5° C. to be maintained during the entire testing procedure, may be achieved as shown here using immersion stirrer-thermostatic equipment (4) with a contact regulating thermometer (5). A horizontal rigid glass-made platform (6), designed to cover completely the water bath (2) and to receive container (1), may preferably be used to fix container (1) in the same specified and stable position and to allow container (1) to be freely removed therefrom at the end of an experiment, so as enable easy withdrawal of all the liquid contained therein and enable exact repositioning of the container before each new testing procedure. This platform is also intended to retard evaporation from water bath (2) and to prevent water spattering into test container (1).

Fabrication of apparatus components (1), (2) and (3) of a transparent material, such as glass, permits convenient observation of the immersed test object throughout the entire measuring procedure. The assembly containing water bath components (1) to (6) is disposed upon suitable damping devices (7) which are themselves placed on an independent suitable shock-proof table, such as a beton base (here not shown), so that no part of the assembly contributes motion, agitation or vibration to the measuring module of the weighing apparatus (9) and so that the solvent (8) filling the container (1) is isolated from external accidental shocks. Also, it is preferred that the entire apparatus exemplified in FIG. 1 and FIG. 2, be placed in a suitable installation site largely free of heat radiation, aggressive or corrosive substances, dust, vibrations, drafts, magnetic fields, static electricity, pressure variation due to room ventilation and similar environmental factors which may perturb the validity of weight measurements.

An electromagnetic balance (9) is positioned horizontally above the container (1) in any convenient manner with regard to its size, shape and to the working conditions and instructions pertinent to the specific type of balance that has been chosen for effecting the resultant-weight measurements. As to the specifications of the electromagnetic balance to be selected, any weighing apparatus equipped with a conventional electromagnetic measuring module may be used. Preferably, the weighing balance will have a electromagnetic module centralizing all the forces transmitted thereon which is accessible, or easily reached preferably underneath the balance, in order to connect a suitable device having the double function of holding test object submerged in container (1) and of transmitting vertically and as a whole the resultant force exerted by the test object. Also, the weighing apparatus should be selected such that its measuring characteristics in terms of readability, accuracy, stability and reproducibility of results, meet the minimum expectations and satisfy all requirements with regard to the quality of measurements needed, the desired weighing range, the type of testing procedure and the nature of the material to be evaluated. It is also preferred that the weighing apparatus measuring module of the balance be equipped with suitable data transmitting means and display and/or recording means, such as a digital data output and recorder. Thus, the weight values provided by the balance and momentarily displayed may be sent automatically and continuously to suitable recording means during the entire measuring procedure when effecting resultant-weight measurements as a function of time.

In one specific embodiment of the invention, chosen solely for illustrative purposes, the weighing equipment used was an electronic toploader Sartorius L420D balance. This electromagnetic weighing apparatus is designed, among other things, for effecting measurements of weights that may be hooked underneath the base plate (16). Also, this balance is equipped with an MP8-4 data input/output interface. It has a dual weighing range of 40/420 g with a respective dual readability of 0.001/0.01 g and may be advantageously used for most single unit pharmaceutical dosage forms in the range of 0 to 40 g with a 0.001 g readability, when measuring a downward force, or from −40 to 0 g with the same readability by subtraction of the tare when measuring an upward force underneath the balance. The standard deviation and the maximum linearity deviation of the measurements are both less than to 0.001 g. Adaptation of the balance to the environment and application requirements may be programmed by selection of the appropriate digital filter, and the stability range may be adjusted to the prevailing conditions via the balance operating program. This equipment assembly fulfills all requirements needed for a system suitable for resultant-weight measurements of pharmaceutical floating and non-floating dosage forms and hence will be used in a detailed description of the invention. However, this particular apparatus, shown in schematic form in FIG. 1 and FIG. 2, is selected for illustrative purposes only and it will be recognized by those skilled in the art that this assembly is applicable to a wide variety of other possible uses and that components of the assembly may be replaced by other suitable and/or comparable electromagnetic weighing means.

Figure 2:
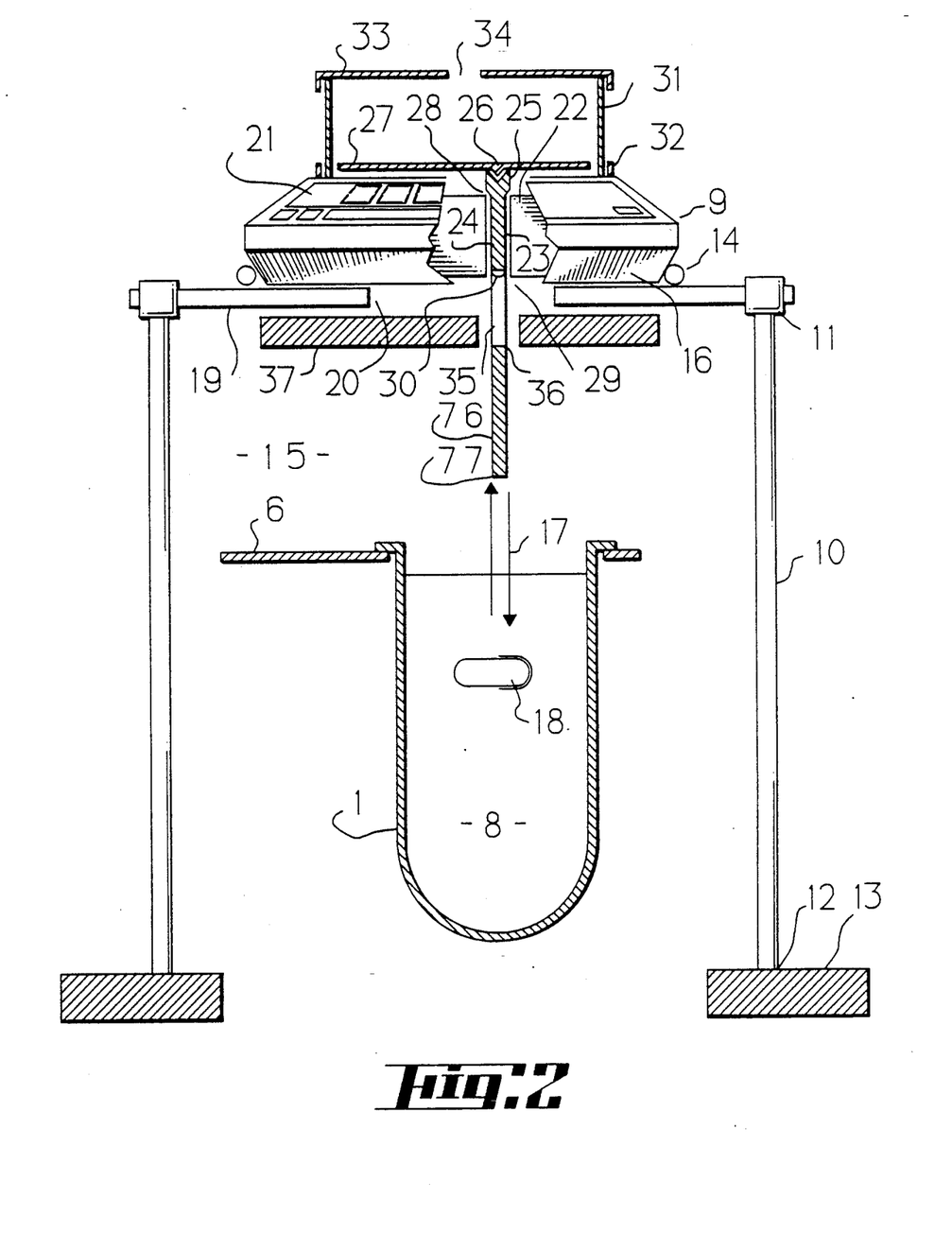
FIG. 2 is a partial central section of the apparatus shown in FIG. 1 with an internal schematic view of the connection between the weight transmitter device and the measuring module of the balance.

In FIG. 2 there is shown a partial view in schematic form of the weighing equipment and adjoining structure according to the invention shown in FIG. 1. A partial central section of the weighing apparatus shows an internal schematic view of the connecting means between the weight transmitter device and the measuring module of the exemplified balance. Suitable means may be provided to fix the balance (9) in a horizontal and stable position above the test container (1) in any convenient manner, such as shown here disposed on a conventional laboratory stand (10) made of a set of rigid and straight stainless-steel tubes having a cylindrical cross-section, and which tubes are firmly and permanently fastened at right angles to each other by suitable clamps (11) of any known type. The top of the structure (19) that supports the balance, as well as the space (15) between the base plate (16) of the balance and the platform (6) of the water bath, should be clear of tubes, clamps or any other obstructing device in order to leave a suitable passageway (20) underneath the balance for downward extending elements such as the weight transmitter device. Structural stability of the assembly of tubes is provided by an adequate number of supporting points (12) being themselves located on any suitable type of shock-proof table, such as here on a beton base (13), that may be contiguous to, but totally independent of, the table upon which the water bath assembly is disposed. The balance (9) in any case should be protected from any motion, agitation or vibration that could be accidentally generated by the environment or by other parts of the apparatus.

Since the balance is, in this instance, placed upon and may be easily lifted from the stand to facilitate withdrawal of the container (1) after each test procedure, additional tubes (14) may be provided at the top of the structure in order to form a lodging frame conforming with the base plate (16) of the balance and thus enabling repositioning of the balance after each displacement thereof. The position of the balance should be fixed in a manner such that any elements of the measuring device connected thereon, and extending downwards as to maintain a test object or material (18) submerged in the container filling solvent (8), should cross the surface of the liquid preferably at a point equidistant from the sides of the container and thus be located centrally in the container (1). In this particular instance, a minimal distance of approximately 10 cm separates vertically the bottom of the base plate (16) from the top of the container (1) to allow facile introduction of the holder extremity (17), here represented as a double arrow, and the test object or sample (18), here represented as a gelatin capsule, into the container without necessitating removal of the balance. This arrangement also suspends the balance (9) at a specified and unvarying height above the test sample (18) and consequently permits better reproducibility during operation. A longer distance than 10 cm between base plate (16) and platform (6) should be avoided inasmuch as an extended length of the weight transmitter device exposes it more to perturbing factors such as drafts and the like. To hold the weighing apparatus above the test container, an open structure made of several tubes, such as the framework assembly herein exemplified, is preferred to any other enclosed structure made of assembled plates. An enclosed structure may promote a moisture increase in the space defined between the base plate (16) and the platform (6) of the water bath and may therefore induce condensation of water onto the measuring elements which extend downwardly from the balance, and consequently falsify measurement data.

A partial internal schematic view obtained by a vertical section in the front panel (21) of the exemplified balance is given in FIG. 2 showing the most prominent components of the apparatus. A core structure (22) is located within the balance case. In reaction to an applied force, and by means of electromagnetic equipment of the balance (not shown) which may consist of several solenoid/magnet devices integral with the core (22), an electromagnetic proportional contra-force is generated to restore the initial equilibrium. The value of the current necessitated to achieve this is integrated by a digital/analog impulse counter which translates in turn this information into proportional value in weight units that may be displayed. The core (22), which in this embodiment fills practically the entire height of the balance, has a central opening defining a cylindrical upright passageway (23) for reception of a cylindrical rod (24) which is enlarged at its upper end to form a receptacle (25) for the weighing pan (27). Core (22) extends downwardly through the lower opening of passageway (23) to an end portion having a semi-annular ring (30) attached to the rod (24). The upper end of rod (24) has a central cone-shaped opening lengthwise therein to receive an identically cone-shaped device that is firmly fixed by its base at an eccentric location point (26) on the underside of the weighing pan (27) in a manner that the pan is stably supported in a horizontal position above the balance case.

The clearance between the rod (24) and the internal surface defining the passageway (23) is such as to permit no significant lateral displacement of rod (24). The upper surface of core (22) near the means defining a circular opening (28) of the central passageway bears against the downwardly facing surface of the upper enlargement of receptacle (25) of the rod (24) for supporting said rod (24) and thereby supporting the entire weighing pan (27). By means of this arrangement, any force exerted on the pan (27) is transmitted throughout the pan receptacle (25) and the rod (24) towards the structure of the core (22) wherein it is compensated and measured. The lower end of rod (24) is accessible underneath the balance through circular opening (29) made in the base plate (16). Weights may be hooked on the ring (30) at the lower end of rod (24). A downwardly directed force applied vertically onto the lower end (30) of rod (24) or applied vertically onto any other point of a suitable downward extension of rod (24) is considered by the measuring module as an equivalent weight being deposited on the pan, and any upward force (thrust) as an equivalent weight being withdrawn from the pan of the balance.

In the balance exemplified in FIG. 2, the lower end at semi-annular ring (30) of rod (24) should be considered as being an effective junction-point for connecting a weight transmitter device. The weighing pan (27) remains usable so that any additional weights may be placed thereon to increase the original tare value before making measurements of upward forces underneath the balance, i.e., weighing by subtraction. The pan is protected from drafts or the like by suitable means, such as shown here with a glass cylinder (31) fitted into a draft protection baseplate (32) and covered by a draft protection lid (33) having perforations (34) for pressure and relative humidity equilibrium purposes. Conventional electromagnetic measuring modules are relatively sensitive to temperature variations and thus suitable insulating means should be provided when effecting measurements with a balance positioned near a heat radiation source. A polystyrene insulating plate (37) placed horizontally underneath the balance helps protect it from heat radiating from the water bath when working above room temperature. The plate (37) may cover the entire surface defined by the base-plate (16) with the exception of a suitable passageway for the weight transmitter device (35).

The weight transmitter device may be provided by any suitable device capable of performing the double function of holding a test object totally or partially submerged at a fixed depth in the test solvent during any suitable period needed to achieve the desired measurements and of transmitting mechanically and as a whole the vertical reacting force originating from the material throughout its own structure up to the measuring module of the balance. The weight transmitter device is connected to the measuring module of the balance so that all applications of a vertical force on the weight transmitter device are perceived by the measuring module with the same readability, accuracy, sensitivity and reproducibility characteristics as a force of identical magnitude and direction applied on the pan. Since the reacting force to be measured is already exerted with a vertical resultant, the transmitting device should preferably be positioned vertically also. The transmitting device may be provided by a short, linear, non-compressible and non-flexible structure, with regard to the magnitude of the vertical force exerted, placed between the immersed test object and the connecting point of the measuring module of the balance, such as illustrated by the double arrow representing the weight transmitter device (17). Thus, the entire resultant force developed by the test object is transferred without formation of disturbing counterforces.

The weight transmitter device typically comprises three different parts, namely, an upper portion in contact with the measuring module of the balance, a lower portion which extends into the solvent and holds the object submerged, and a middle portion making a suitable junction between the upper and lower portions The upper portion consists of a suitable structure connected at one end to a selected junction-point of the measuring module and on the other end to the intermediate portion of the weight transmitter device. The upper portion is fabricated of such material and is of such design as appropriate to the selected junction-point and to the working conditions of the measuring module. In the present embodiment, the upper portion of the weight transmitter device consists of a cylindrical solid rod (35) made of rigid material which is also non-magnetizable, non-conducting of current and non-absorbing of humidity, such as PTFE-Teflon plastic. The rod (35) has the same diameter as the lower end of brass rod (24) and an approximative length of 3 cm, which length allows isolation of the electromagnetic measuring system of the balance from metallic pieces of the lower structure. Lower end of rod (24) and its ring (30) have complementary mating surfaces with the upper extremity of Teflon rod (35) to provide a rigid connection.

The weight transmitter device intermediate portion consists of any suitable connecting means making a junction between the upper and the lower portions of the weight transmitter device. The intermediate portion is of adequate dimensions to extend the weight transmitter device downwardly a suitable length in order to place a portion of the holder extremity at a desired immersion depth in the test solvent. The intermediate portion is made of a material which is preferably non-absorbing of humidity, has a in-significant thermic dilatation coefficient and which is able to provide rigidity and firmness in the structure. This intermediate portion should be connected at each of its ends in any suitable steady manner that may confer immobility to the entire device and still allow facile and frequent dismantling for exchange purposes or for operation of the weighing function. In the present embodiment, the intermediate portion of the weight transmitter device comprises a cylindrical solid stainless-steel shaft (76) which is positioned vertically lengthwise, has the same diameter as the upper portion and an approximate length of 6 cm, so that its lower end (77) extends far enough above the liquid surface to avoid penetration of test solvent (8) into the junction. Connections of this intermediate portion with the upper and lower portions are realized by means of a male and a female screw-coupling device threaded into the material at each end of the intermediate portion and the opposing ends of the upper and lower portions connected thereto.

The lower portion, also called the holder extremity, consists of any suitable means connected o one end to the intermediate portion and terminating at an opposite end within the solvent to hold a test object submerged at the desired immersion depth in a convenient manner. The lower portion is interchangeable with components of equivalent function but differently designed to adapt the weight transmitter device in its holding function to varying natures, shapes and sizes of test objects, to different test solvents and to various working procedures. The holder extremity is fabricated to be unaffected by perturbing forces that may be generated by sources other than these participating to the resultant-weight of the test object, or, with respect to the test object, to introduce no perturbing effects upon the original behavior of the test object or its interactions with the test solvent. This lower portion is preferably connected to the intermediate portion above the liquid level and is of unitary construction, or is composed of a small number of pieces tightly connected to each other in order to ensure rigidity of the structure and avoid penetration of solvent into the junction-points during immersion. The non-immersed part of the holder extremity should also preferably not have any horizontal element of relatively large area placed above the liquid level since this may facilitate condensation of solvent vapor or steam onto the device and hence falsify measurement data.

In FIG. 3, there is shown a view of four different examples of holder extremities, designated A, B, C and D, that may be appropriate to pharmaceutical applications for measurement of the resultant-weight of an immersed dosage form or its variation as a function of time. The described holder extremities are made of solid stainless-steel pieces soldered together to form a rigid assembly which is entirely coated by a 30 micrometer thick FVD-Teflon film. Any other suitable rigid material may be used, however, which is non-absorbing of humidity, non-porous, has a non-significant thermic dilation coefficient, is corrosion resistant and has no physical and/or chemical perturbing interactions with either the solvent or the test object. Dimensions in cm given in FIG. 3 are adequately proportioned to hold conventional single-unit dosage forms and are only disclosed for illustrative purposes with respect to this specific application. For each of the four different types of exemplified holder extremities, the vertical cylindrical shaft (38) has the same diameter as the middle portion of the weight transmitter device upon which it is connected as previously described for the screw-coupling extremity (39). The shaft (38) extends linearly downwards to a waist (40) cut therein, which provides an adjusting mark for the liquid level. For each exemplified holder extremity, an identical distance separates the waist (40) and the level point (41) where the test object is positioned, thus ensuring a reproducible immersion depth of the test material for each of the holder extremities.

Figure 3A:
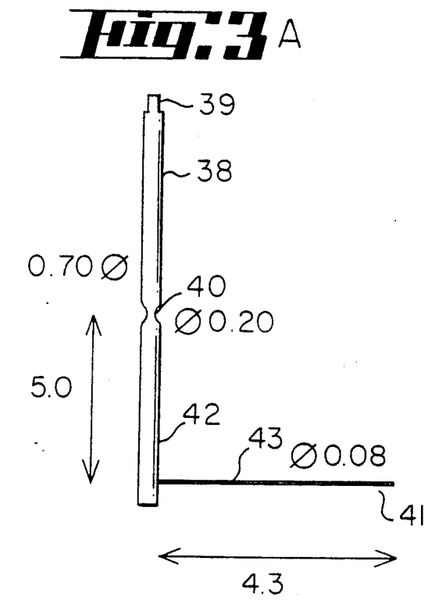
FIGS. 3A-3D are enlarged views showing four examples of holder extremities attachable to the weight transmitter device.

The A type structure, also called the spit-holder extremity, consists of a further downward vertical extension (42) of shaft (38) having inserted and soldered at a right angle near the lower end a sharp, solid needle (43) to hold immersed any test material that may be placed thereon.

Figure 3B:
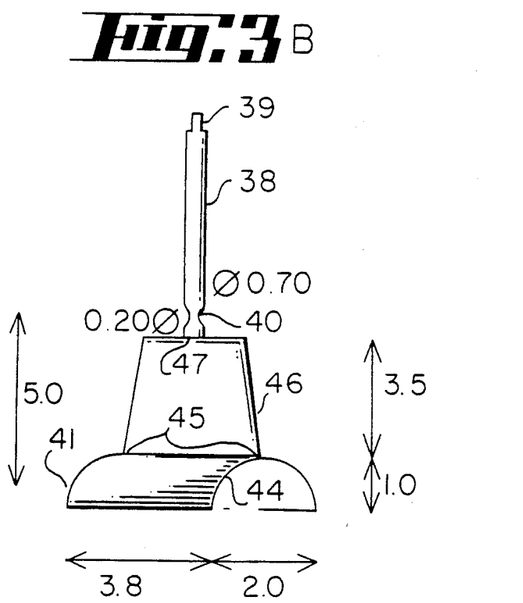

The B type structure, called the basket-holder extremity, consists of a semi-cylindrical shaped wire-mesh basket (44) of an 8-mesh size positioned horizontally lengthwise with its concave side facing downwards. Basket (44) is firmly clamped by soldering means at each of its top edges (45) to a U-shaped bridge (46). Shaft (38) is firmly fixed at a centrally-located attachment point (47) on the horizontal upper portion of U-shaped bridge (46). Any test object having a bulk density lower than the density of the solvent in which it is submerged may be maintained below the liquid surface using the concave side of this basket-holder extremity.

Figure 3C:
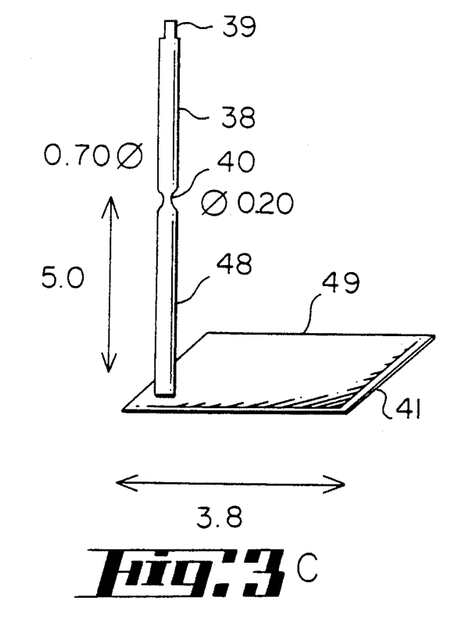

The C type structure, also called the pan-holder extremity, consists of a further downward vertical extension (48) of shaft (38) whereon, at its lower end, an 8-mesh size wire-mesh pan (49) is soldered at right angle near the center of an edge. Any test object having a bulk density higher than the density of the solvent in which it is submerged may be deposited upon the upward facing side of the mesh pan and so be maintained below the liquid surface.

Figure 3D:
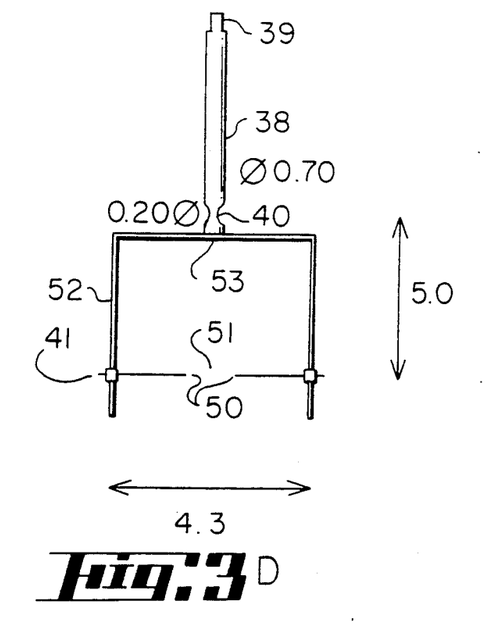

The D type structure, called the grip-holder extremity, consists of two sharp, solid needles (50) disposed horizontally in lengthening extension so that the opposing needle-points define an appropriate space (51) therebetween. Needles (50) are firmly soldered at right angles and at their distant extremities to a U-shaped bridge (52) that makes suitable connection between the needles (50) and the shaft (38) fixed to a centrally-located attachment point (53) on the U-shaped bridge (52) by its horizontal upper portion. This holder extremity holds immersed any test material that may be gripped between the needles.

Each of these exemplified holder extremities may have differing effects on a specific test material when maintaining it immersed, so that the holding capabilities and also the perturbing actions that these devices could exhibit during their uses may differ from one type of structure to another. It is, for example, usually apparent that an increase in contact-points between the test material and the holder improves the holding capabilities thereof but consequently increases its obstructing action and hence reduces proportionally the original and normal interaction between the test material and the solvent. The design and the choice of such optimal holder extremity to be utilized in one specific occasion is considered to be within the purview of one skilled in the art.

The embodiment of the invention shown in FIG. 1 is given only for illustrative purposes. With reference to the drawings, a conventional floating capsule (18) is shown conveniently maintained submerged in the test solvent (8) by the basket-holder extremity (54) which is already connected to the other parts of the structure up to the measuring module inside the balance (9) in a suitable manner as disclosed herein. The entire weight transmitter device is shown in its proper position with the waist (40) being adjusted at the same level as the liquid surface. Since the buoyant force in the solvent (8) is also acting on the submerged basket-holder extremity (54) of the weight transmitter device (35) with a magnitude that is proportional to its immersed volume, any level variation of the solvent contained in vessel (1) changes the value of the immersed portion and modifies the apparent weight measured by the balance. Therefore, the waist (40) may not only be considered as an adjusting mark but is also an efficient tool, in view of reduction of the shaft diameter at the air/solvent interface, to reduce the variation of the immersed volume of the holder for each equivalent liquid level variation and hence to minimize the magnitude of the weight drifts that may be recorded by the balance when the liquid level varies Significant weight drifts may be expected due to a continuous liquid level decrease by evaporation of the solvent during a kinetic measuring procedure. It is not desirable, however, to place a cover above container (1) to retard evaporation as such cover may promote condensation of solvent vapor or steam upon the non-immersed part of the weight transmitter device and upon the internal side of the cover, with a consequent introduction of drops of condensation which would have perturbing effects on measurements. Hence, suitable solvent level compensating means should be provided in order to bring any perturbance introduced by evaporation automatically under control, such as with the constant liquid level regulating system hereinafter described.

As shown in FIG. 1, a suitable stock vessel (55) is provided to contain a solvent (56) preferably identical to that used in container (1) and in such quantity as appropriate for the duration of the measuring procedure. A central opening (57) made in the bottom of said stock vessel (55) is connected, by suitable clamp means, to a hose or conduit (58), of either a flexible or rigid tubing. This conduit (58) leads from the bottom of said vessel (55) to the inlet (59) of solvent flow control means that are provided for causing alternatively an interruption or a starting of the flow of solvent within conduit (58). In the particular embodiment here used for illustrative purposes, an electro-valve (60) is shown of type Herion 2/2-DN1 made of stainless-steel and FKM-Viton. From the outlet (61) of valve (60) extends a further identical conduit (62) leading to container (1) wherein conduit (62) dips vertically downwards close to the edge thereof and to the bottom. A suitable distance separates the stock vessel (55) and container (1) whereby, after opening of the valve (60), appropriate flowing action may be obtained inside the conduits (58) and (62) without necessitating pumping means. The entire stock solvent circuit should be made of materials which are inert to the liquid being handled therein. Suitable level detection means are provided and current supplying means are linked thereto in any manner so that the electro-valve (60) may be automatically driven in proper position at each significant level decrease of solvent (8) and that the loss of solvent by evaporation may be continuously compensated. For this instance, a pair of electrodes (63) is positioned stably above container (1) with their lower extremities immersed at different and fixed depth into the solvent. The electrodes are here made of stainless-steel introducers taken from spinal tap needles and have a 0.2 mm diameter, but they may be replaced by other suitable means. The lower end (64) of the higher electrode (65), which should preferably be connected as a cathode, just contacts the liquid surface and determines therefore the height of the liquid level into container (1), while the anode (66) may be immersed more deeply as desired. These two electrodes are connected to suitable current supply and electronic means, such as a signal amplifier (67), in order that a microvoltage should travel through the circuit made by the solvent (8), the electrodes (63) and the signal amplifier (67). Any level decrease which interrupts the current passage in the circuit is systematically detected by this signal amplifier (67), which in turn commands the power supply module (68) of the electrovalve (60) to open the valve and allow flow of the solvent from stock vessel (55) into container (1), until the current passage is restored and consequently the liquid level is re-established. Suitable fastening means may be provided to fix conduit (62) and the electrodes (63) above container (1) in any appropriate and non-obstructive manner that permits normal immersion of the test object and the measuring devices. The stock vessel (55) may also be jacketed for temperature control purposes but this should usually not be necessary where small amounts of stock solvent are delivered regularly into container (1). The regularity and hence the quality of compensation in function of time, i.e., the small amount of solvent additions at the shortest time intervals, may be improved by reducing capillary phenomenon of the extremities at the level of the detecting electrodes, such as here by using sharp-pointed electrodes. Also, a suitable amount of an appropriate surface-acting agent may be added to the solvent in order to reduce the magnitude of the surface tension in container (1). If desired, several devices according to the present liquid level regulating system may be adjacently located within housing (69).

In addition to the electromagnetic measuring module, suitable recording means are provided and may be connected therewith in any convenient manner that enables an automatic and permanent record of the resultant-weight measurements carried out by the balance as a function of time. Suitable recording means are provided by an MP8-4 digital data output interface of the Sartorius L420D balance connected to a digital/analog 7287 Sartorius converter (71) by means of an appropriate connecting cable (70) for full duplex digital data transfer. Once suitably programmed with respect to the working conditions of the balance, the converter is able to produce automatically a continuous data transfer from the balance and to convert simultaneously into proportional analog voltage the digital values corresponding to the weights displayed by the balance The resulting analog information is available, synchronous to the display, in different voltage range selections (72) and may be transferred into any appropriate analog recorder by means of a suitable cable (73). The resulting analog voltage provided by the converter is here transmitted into a Goerz Metrawatt Servogor 120 x/t paper recorder (74) which ensures an uninterrupted plotting of the results without need of any manual intervention of an operator during the entire measuring procedure. The desired digital/analog conversion may be obtained by selecting the appropriate position from three decade selections (75) anywhere within the decade range of the converter (71), such as here shown, for example, by converting 1.000 g into 1.000 volt with a readability of 1 mg=1 mV. In the same way, as and if desired, the readability and sensitivity characteristics of the x/t recorder may be freely fixed as required by the type of measuring procedure to be achieved, such as floating dosage form measurements, by covering the 0 to 100% plotting scale of the recorder with a 0 to 100 mV or a 0 to 1000 mV voltage input range scale, which signifies that a 1 mg weight should thus be recorded respectively as a 2.5 mm or a 0.25 mm deflection of the recorder pen (76). Regarding the time base-line characteristics, selection is made between the twelve possible paper speeds ranging from 1 cm/h to 60 cm/min so that the time running should be the most appropriate to the total duration of the measuring procedure and to the readability needed to interpret time events retrospectively.

OPERATION OF THE INVENTION

Starting with the parts assembled and connected as shown in FIG. 1, but with no solvent in container (1) and without a test object (18) being maintained by the holder extremity (54), the apparatus may be made ready for a conventional resultant-weight monitoring experiment by allowing at least 1 hour warmup to the balance (9) after connection to the line power, for weighing stability purposes. The holder extremity (54) may be unscrewed from rod (35) at junction point (36) by relative rotary motion with respect thereto and be cleaned or replaced by another if desired. If removal of container (1) is necessitated for cleaning purposes, such removal should be carried out during the withdrawal of the holder extremity. Also, the balance may be displaced to facilitate removal of container (1). After replacement of the container and correct repositioning of the balance using the suitable means disclosed, the selected holder extremity (54) should then be adequately refastened into proper position at rod (35). The readability and sensitivity characteristics required by the present experimental procedure should then be selected and programmed. Temperature of the water bath (2) may then be adjusted to the experimental conditions by means of the immersion stirrer thermostatic arrangement (4), while the desired amount of selected solvent (8) is added to container (1) and left therein for a suitable temperature stabilization period. In the meantime, the desired amount of the selected stock solvent (56) may be added to the stock vessel (55), the solvent (56) having ordinarily the same characteristics as solvent (8) filling container (1), and the amount being at least enough to compensate for the loss of solvent (8) by evaporation throughout the entire experiment. The liquid level regulating system (69) is started and the stock solvent (56) thus flows into conduits (58) and (62) and into the electrovalve (60) up to the lower end of the circuit. After suitable air purging of the entire stock solvent circuit, the liquid level regulating system is momentarily stopped and left standby with the electrovalve (60) being in closed position.

Details about the nature and specifications of all the solvents that may be used to fill the test container (1) are not given inasmuch as this may be of any known type and may be freely selected from aqueous/ non-aqueous liquids and water-in-oil/oil-in-water mixtures according to the particular kind of material to be tested and the needs of the testing procedure. The solvent should not, however, absorb, react, or interfere, if not intended, with any of the materials of the apparatus to be in contact therewith. Achieving a stable and reproducible base-line record when effecting continuous resultant-weight measurements as a function of time may be difficult since aqueous solvents may in some occasion generate measurement disturbances. Thus, several guidelines should be observed as to specific measuring procedures appropriate to follow for pharmaceutical dosage forms to be tested in pharmaceutical aqueous media that are intended to represent in vivo conditions during in vitro tests, e.g., hydrochloric acid solution of pH 1.2, simulated gastric fluid or simulated intestinal fluid.

After immersion in an aqueous solvent, the submerged portion of the holder extremity may progressively entrap a variable amount of air bubbles which are released from within the solvent. This may cause in turn an important and aleatory base-line weight drift when effecting measurements as a function of time and hence may introduce erroneous results. The perturbance by adherence of air bubbles onto the weight transmitter device may be brought under control by using an aqueous solvent made of air-free water which should preferably be prepared before the experiment by suitable means well known in the art. Additionally, a reduction of the magnitude of surface tension exerted in the solvent (8) may diminish further the possibility of air bubble adherence onto the immersed portion of the holder extremity and onto the test material. In order to secure the quality of measurements, a suitable amount of an appropriate surface acting agent may therefore be added into the aqueous solvent, such as 0.05% of Tween 80, to fix from the start a low surface tension value for the solvent and consequently minimize the possible effect of a surface tension variation on the holder extremity and the weight measurements, or also to obtain in turn an identical value of surface tension as shown by the gastric fluids.

The amount of test solvent (8) to be used should be that amount necessary for immersion of the test sample. In kinetic test procedures of resultant-weight measurements where a substantial denaturation either in the size, shape or nature of the test material is expected as a function of time, such as dissolution or melting, the volume of solvent should preferably be large enough and appropriate as to not impede normal interaction between the test object and the solvent throughout the entire measuring procedure and not modify the normal progress of denaturation. In the particular application of pharmaceutical single-unit dosage forms, here taken for illustrative purposes, a volume of 1000 to 1200 ml solvent may fill adequately the USP container (1) so as to accommodate solubility saturation or significant fluid density variation. The volume should be adjusted so that the solvent level (8) coincides with the smallest diameter vertical portion of the waist (40) cut in the holder extremity (54). After filling container (1) with the selected solvent (8) up to nearly the desired level, the level detecting electrodes (63) should be positioned so that the fine adjustment of the liquid level may be realized precisely and automatically with the stock solvent by means of the liquid level regulating system. Since immersion of the test material into the solvent (8) will elevate the liquid level in the container (1), fine adjustment of the liquid level should preferably be carried out after complete immersion of the solid material to be tested. Two different types of immersion procedure may, for example, be used. In the first procedure, the test material is immersed into the solvent by suitable means, such as with tweezers, up to the depth where it should be placed and is immediately left free to react against the holder extremity. The liquid level is adjusted by starting the regulating system and, after zero the display of the balance, the recorder is switched on. In the second procedure, the test material is immersed into the solvent by suitable means, such as with tweezers, and is maintained momentarily submerged just below the surface and beside the holder extremity while the liquid level is adjusted by starting the regulating system and the display of the balance is set to zero. The test material is then brought up to the desired depth and is left free to react against the holder extremity After switching on the recorder, the resultant-weight value produced by the test material may be taken from the display of the balance or calculated from the deflection made by the pen of the recorder.

The following examples further illustrate the invention:

EXAMPLE NO. 1

In a specific test, the apparatus here described was employed for measuring the resultant-weight of different solid materials of known weight and volume in order to compare the results given by the invention with the respective theoretical values obtained by calculation (Equation 3). Table I shows the characteristics and dimensional data of three different spherical materials (Solids No. 1, 2, 3) having a specific gravity higher than one and three different tubular materials (Solids No. 4, 5, 6) having a specific gravity lower than one.

TABLE I

| Solid No. | Material | Volume (mm3) | Specific Gravity | Resultant-weight (mg) | |
|---|---|---|---|---|---|
| | | | | Calculated | Measured Mean ± SD |
| 1 | Inea glass | 2,066.8 | 2.3957 | −2,890.1 | −2,890.3 ± 0.9 |
| 2 | Inea glass | 2,000.4 | 2.3966 | −2,798.9 | −2,797.5 ± 0.5 |
| 3 | Stainless-steel | 530.7 | 7.6863 | −3,549.8 | −3,549.8 ± 0.4 |
| 4 | Teflon | 1,078.4 | 0.5326 | 501.2 | 500.4 ± 0.5 |
| 5 | Teflon | 2,648.1 | 0.8886 | 287.9 | 289.1 ± 0.7 |
| 6 | Teflon | 5,155.2 | 0.7826 | 1,107.3 | 1,108.8 ± 0.8 |

The solid materials were measured utilizing the apparatus shown in FIG. 1, without the continuous recording means connected to the balance The solvent used was 1200 ml water and 0.05% Tween 80, thermostatically maintained at 25.0° C. and in which the weight transmitter device was assembled with the basket-holder extremity (B) shown in FIG. 3. Each different solid material was assayed 10 times in a randomized manner. The spherical materials 1, 2 and 3 were deposited above the basket exerting a downward resultant thrust when dropped into the solvent (specific gravity higher than one) and tubular materials 4, 5 and 6 were left under the basket exerting an upward resultant thrust when dropped into the solvent (specific gravity lower than one). Before each assay, the solid material was cleaned, dried and temperature stabilized at 25.0° C. before immersion. After readjusting the level of the solvent at a fixed height using the automatic compensating system herein described and after setting the display of the balance at zero, the already immersed solid material was left free to react against the holder extremity of the weight transmitter device. The resultant-weight value displayed by the balance with a 1 mg readability was then recorded manually.

Averaged results given in Table 1 show an excellent correlation for all solid materials between experimental results and the theoretical resultant-weight values obtained by calculation. Such correlation shows that the original calibration and the accuracy of the measuring module of the balance are not modified when the weight transmitter device is connected. The standard deviation values associated to the mean resultant-weight results of each test object indicate the appropriate reproducibility of measurements. The measurements provided by the invention are also in accordance with the definition of the resultant-weight as noted in Equation 3.

EXAMPLE NO. 2

This example illustrates the stability and the reproducibility of the measurements obtained during a continuous record of the resultant-weight values measured by the apparatus as a function of time.

The experimental procedure was realized by means of the apparatus schematized in FIG. 1 wherein the solvent was 1200 ml air-free HCl pH 1.2 and 0.05% Tween 80 thermostatically maintained at 37° C. and in which the weight transmitter device was assembled with the spit-holder extremity (A) during the first part of experiments and with the basket-holder extremity (B) during the second part of experiments (both holder extremities being shown in FIG. 3). Operation of the apparatus was conducted with respect to the directions and working conditions disclosed by the invention and in accordance with the hereinbefore exemplified operating procedure with the one exception that, after zero adjustment of the display of the balance, no test material was immersed into the solvent and placed against the weight transmitter device In such context, the absence of significant variations of the recorded resultant-weight value should indicate that all systematic and/or aleatory interfering factors that may affect the stability of measurements in function of time are brought under control by the apparatus of the invention. Readability and sensitivity of recording means were fixed prior to the test in such a manner as to be able to disclose any weight drift of the measuring system during the experimental procedure (conversion 1 mg=1 mV=2.5 mm, paper speed: 3 cm/hour). After each assay of a 12 hours recording period, the entire apparatus was disexperimental connected, the vessel content was withdrawn and replenished by fresh solvent, and a new measuring procedure was restarted in accordance with the hereinbefore described operating directions of the invention.

Figure 4A:
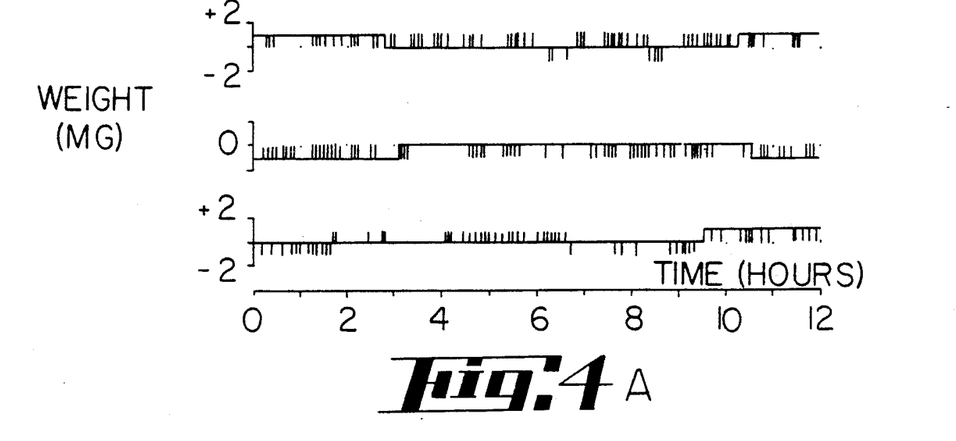
FIGS. 4A-4C are a set of graphs showing stable and reproducible base-line records of resultant-weight measurements made as a function of time obtainable with the apparatus and method of the invention and described in Example 2.
Figure 4B:
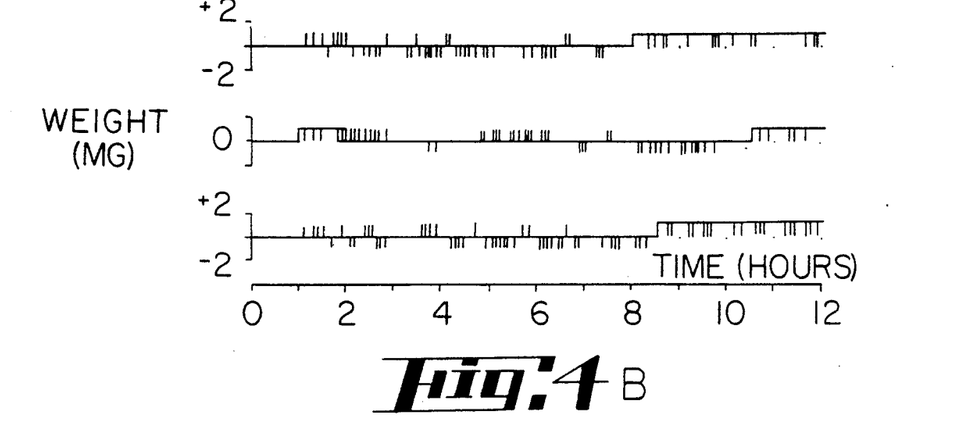

The baseline resultant-weight curves obtained as a function of time during three typical measuring procedures with the spit-holder extremity (A) and during three typical measuring procedures with the basket-holder extremity (B) are shown in FIG. 4, with all base-lines (A) and (B) ending at 12 hours inasmuch as the experiments were ended at that time.

Another experimental procedure was conducted in order to compare the stability and the reproducibility obtained from the apparatus and the method of the invention with the stability and the reproducibility that may be obtained when setting to work only the balance embodying the invention in its original state such as provided by the manufacturer. This balance, non-assembled with the weight transmitter device, was connected to the recording means and the continuous base-line weight measurements were recorded in function of time.

Figure 4C:
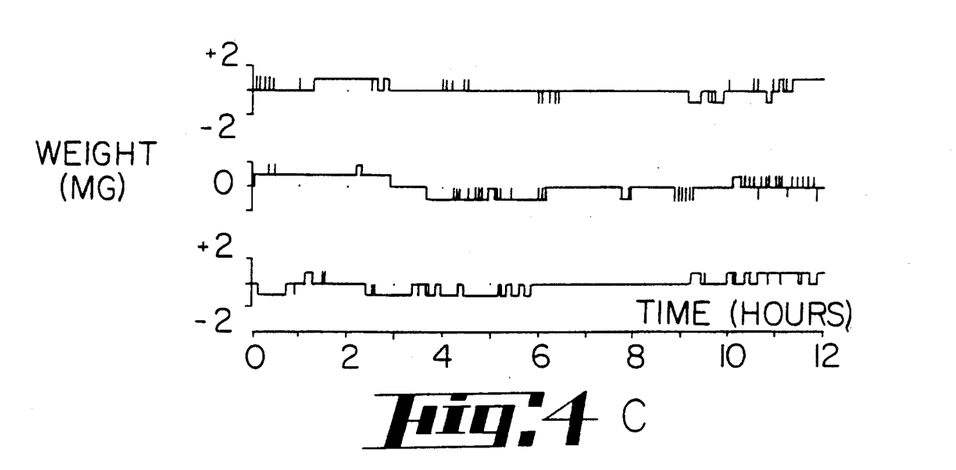

The base line weight curves obtained during three typical 12 hours measuring procedures with the unmodified balance are shown in FIG. 4 (C).

As appearing from observation of curves (A) and (B), the stability in function of time of the measurements provided by the invention is attested in all cases by obtaining a linear resultant-weight base-line record throughout the entire measuring procedure. The linearity deviation of these base-lines is of maximum 2 mg and no resultant-weight drifts greater than $\pm 2$ mg are observed during at least 12 hours. When compared to the base-lines (C) obtained before modification of the balance, the magnitude and the frequency of weight drifts shown by the base-lines of the invention are seen to be within the normal range of variation for such measuring systems and the stability of measurements made in function of time is considered to be unaltered by the modifications brought to the balance. Moreover, FIG. 4 also indicates that reproducibility of comparable base-line records using either a spit-holder extremity (A, n=3) or a basket-holder extremity (B, n=3).

It may therefore be stated that the invention is providing an apparatus and a method wherein all systematic and/or aleatory interfering phenomena that may occur during the measuring procedure and may affect the quality of measurements are automatically brought under control and do not perturb significantly the original readability, accuracy, sensitivity and stability of the measuring system, whether these phenomena are of intrinsic origin (e.g. magnetization of measuring module, temperature increase inside the balance, solvent evaporation, dissolved air in solvent, bubbles trapping by weight transmitter device, steam condensation, surface tension variation in solvent, etc.) and/or of extrinsic origin (e.g. agitation, vibration of measuring module, drafts, over-pressure of room ventilation, etc.).

Consequently, by supplying stable and reproducible resultant-weight base-line measurements throughout continued experimental procedures, the apparatus and the method according to the invention are providing, in the presence of an immersed test material, resultant-weight curves which are rigorously reflecting in function of time the exact and precise behavior in terms of resultant-weight variation of the said test material.

EXAMPLE NO. 3

For comparative purposes, four different sustained release formulations were prepared as set forth in Table II and the four homogeneously blended mixtures were filled into No. 1 size clear hard gelatin capsules.

TABLE II

| Ingredient | Percent in formulations | | | |
|---|---|---|---|---|
| | A | B | C | D |
| Sodium riboflavin 5'phosphate | 1 | 1 | 1 | 1 |
| Methocel K4M (*) | 20 | 30 | 50 | 70 |
| Lactose 100 mesh | 79 | 69 | 49 | 29 |
| Total weight (mg)/capsule | 352 | 326 | 284 | 245 |

(*) hydroxypropylmethylcellulose 4000 cps

The capsules made of these four different sustained release formulations are suitable for oral administration and are hydrodynamically balanced to have a bulk density of less than one in contact with gastric fluid. Capsules of A, B, C and D type have been found to remain buoyant in vitro over a certain period of time when dropped into a vessel containing simulated gastric fluid USP maintained at 37.0° C. The capsules were tested one by one utilizing the apparatus here described and shown in FIG. 1. The solvent volume was 1200 ml aqueous HCl at pH 1.2, with 0.05% Tween 80, maintained at 37.0 ° C. The weight transmitter device was assembled with the spit-holder extremity (A) shown in FIG. 3. Readability and sensitivity of recording means were adjusted prior to assay to standard conditions for floating dosage form measurements (conversion 1 mg = 1 mV = 0.25 mm, paper speed: 3 cm/hour). After each assay, the vessel contents were withdrawn and replenished by fresh solvent. The capsules remained spitted lengthways on the holder extremity throughout the entire measuring procedure. The comparative resultant-weight mean curves for these tests (n = 3 for each type of formulation) appear in FIG. 5 with lines A, B, C and D showing respectively the resultant-weight records as a function of time of capsules A, B, C and D. The line A ends at 1 hour, B at 4 hours, C and D at 8 hours inasmuch as the experiments were ended at that time. The dotted line represents an 8 hour resultant-weight mean curve (n = 3) obtained after effecting the same measurements as hereabove described using the same apparatus and operating conditions except that no capsule was spitted on the holder extremity. For each tested capsule, the resultant-weight value measured by means of the invention just after immersion of the capsule and before dissolution of the gelatin is equal to the resultant-weight value that can be obtained by calculation when knowing the weight and the external volume of the dosage form and the density of the solvent (Equation 3). The capsule is, from the start and throughout the entire procedure, maintained firmly at the same immersion depth by the spit of the weight transmitter device and so, as hereinbefore disclosed, that perturbing factors do not affect the stability of the apparatus and the exactness of the measurements. Thus, the continuous curves provided by the invention and shown in FIG. 5 may therefore be considered as representing a continuous succession in time of the exact resultant-weight values of the tested capsules.

Figure 5:
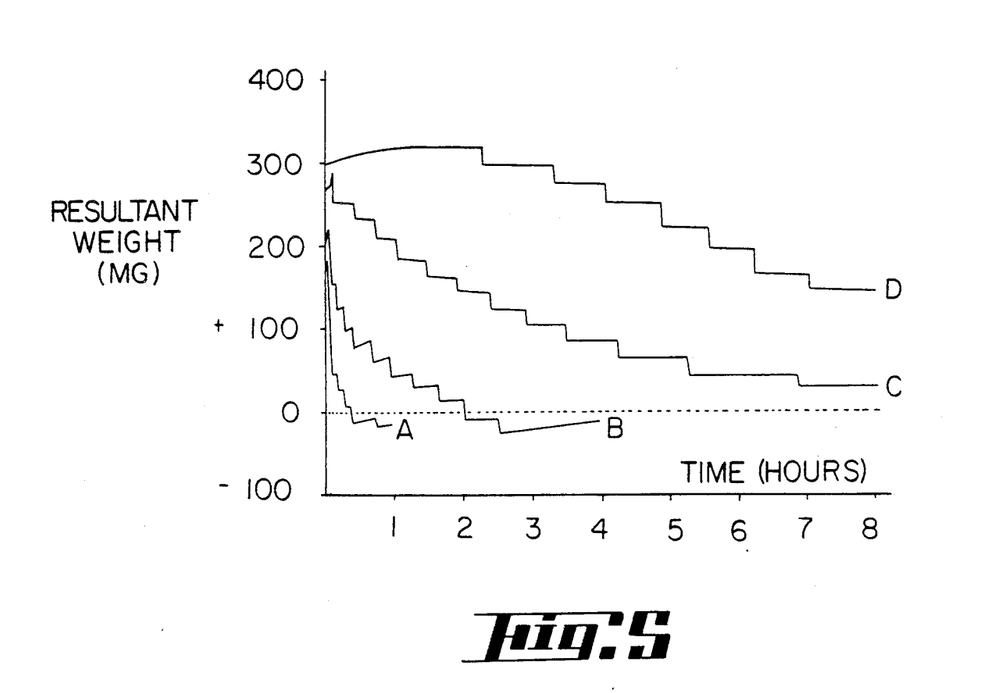
FIG. 5 is a graph illustrating the operation of the apparatus when effecting measurements as a function of time on the floating dosage forms described in Example No. 3.

These measurements can help determine important and critical characteristics of the floating dosage forms. Firstly, a floating duration can be accurately determined after experimentation for each capsule by measuring the moment at which the resultant-weight curve crosses the zero base-line (density of test object = density of fluid) and changes its sign from positive to negative. As shown in FIG. 5, the mean floating duration of capsule A is about 21 minutes, of capsule B is about 108 minutes and of C and D is greater than 8 hours. The precision of this determination depends only on the nature of the recording means and the fixation of their working parameters (for example, paper speed of x/t recorder). Secondly, for capsules that do not sink within the measuring procedure, the examination of the data may disclose comparatively different floating capabilities between the tested dosage forms. This may be confirmed more accurately by measuring and comparing the respective area under the curve (AUC) values of the resultant-weight measurements as a function of time. For example, as shown in FIG. 5, the capsule D exhibits higher resultant-weight values in time and is therefore considered as having better floating characteristics than capsule type C. The measured mean AUC values from 0 to 8 hours are respectively of 725 mg. hour for capsule C and 2073 mg. hour for capsule D. Thirdly, examination of the resultant-weight curves concurrently with the observation of the dosage forms in the vessel during the measuring procedure may help in understanding some of the phenomena affecting the resultant-weight of a dosage form during its immersion in an appropriate solvent. For example, the step-wise changes denoted by the curves of FIG. 5 each correspond to the release of an air bubble from the capsule, which release produces a consequent loss of floating strength (abrupt resultant-weight decrease). As shown in FIG. 5, the better floating capabilities of capsule D compared to C are related to a less frequent release of air bubbles after immersion. As shown in Example No. 3, the spit-holder extremity device, adapted for non-disintegration of the "hydrodynamically-balanced system" (HBS) type capsules of type A, B, C or D, holds the dosage forms spitted lengthways during the entire measuring procedure with no significant deterioration of the test sample. The two points of contact with the formulation enable complete and normal interaction between the test material and the solvent, and promote achievement of correct measurements since there is minimum surface of securing means that may retain solid particles left by erosion or that may entrap the air bubbles released from the formulation.

EXAMPLE NO. 4

Figure 6:
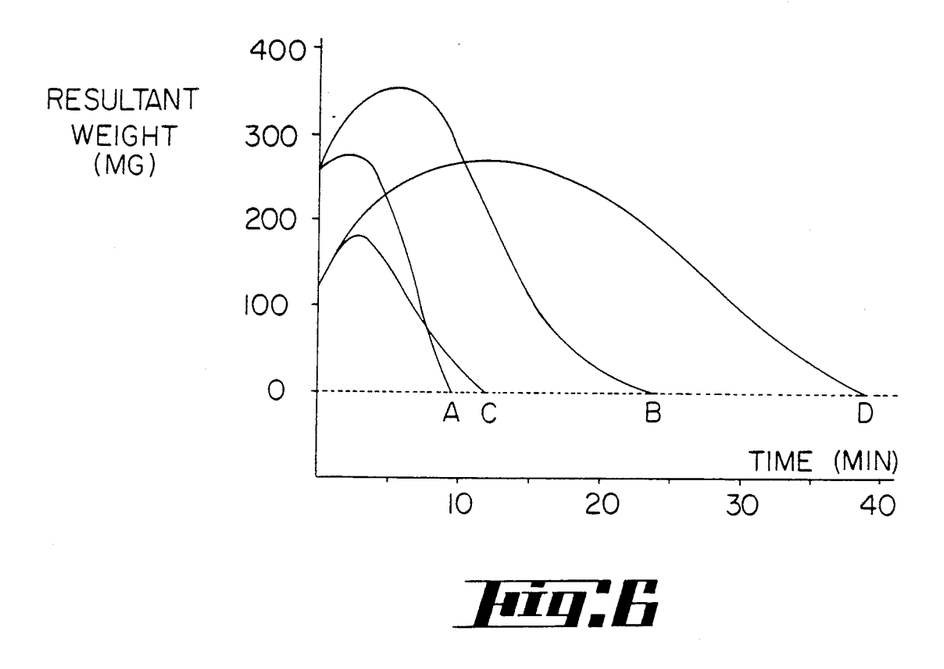
FIG. 6 is a graph illustrating the operation of the apparatus when effecting melting kinetic measurements of the fatty base suppositories described in Example No. 4.

This example illustrates the operation of the apparatus for effecting resultant-weight measurements on suppositories Identically shaped adult suppositories were prepared by a conventional pharmaceutical moulding technique using two different types of pure fatty bases well known in the art, i.e., Witepsol W35 and Suppocire AS2X. The suppositories made of these pure fatty bases are suitable for rectal administration but do not contain any pharmacologically active substance. For comparisons purposes, Suppocire AS2X suppositories were tested immediately after preparation (type A) and after 12 month storage at room temperature (type B), and Witepsol W35 suppositories were tested immediately after preparation (type C) and after 12 month storage at room temperature (type D). The thus formed suppositories were tested one by one utilizing the apparatus here described and shown in FIG. 1., in which the solvent volume was 1200 ml water at pH 7.0, containing 0.05% Tween 80, and maintained at 37.0° C. The weight transmitter device was assembled with the basket-holder extremity (B) shown in FIG. 3. After each essay, the vessel contents were withdrawn and replenished by fresh solvent. The suppositories remained positioned lengthways under the mesh basket until total liquefaction of the fatty base. The comparative resultant-weight curves for these tests appear in FIG. 6 with lines A, B, C and D showing respectively the resultant-weight records as a function of time of suppositories A, B, C and D. These curves represent the melting profiles of the tested fatty bases and may be further analyzed to determine comparative characteristics of the products. Termination of lines A, B, C and D at the zero base-line signify the total liquefaction of all the suppositories. These time-points may therefore be considered as the exact liquefaction time of the tested suppositories, i.e., 10 min and 24 min for the Suppocire AS2X suppositories tested immediately or after one year, and 12 min and 40 min for the Witepsol W35 suppositories tested immediately or after one year. The foregoing experiment demonstrates the manner in which the invention provides useful data as to the aging characteristics of pharmaceutical formulations, which data help determine the design of shelf-stable formulations

EXAMPLE NO. 5

This example illustrates the operation of the apparatus while effecting resultant-weight measurements on various film-coated capsules in order to determine the permeability thereof to gastric fluids as a function of time.

For comparative purposes, two different gastro-resistant film-coating formulations (A) and (B), both containing a same percentage of CAP, were prepared as set forth in Table III. Test capsules were sampled from a homogeneous batch of No. 0 size clear hard gelatin capsules filled volumetrically with lactose 100 mesh up to a total weight of 630 mg (bulk density: 0.7409). The test capsules underwent once, twice or three times a coating process by one of two formulations (A) or (B).

TABLE III

| Formulation (A) | | Formulation (B) | |
|---|---|---|---|
| Cellulose Acetyl Phthalate | 10% | Cellulose Acetyl Phthalate | 10% |
| | | Diethyl Phthalate | 2% |
| Acetone | 90% | Isopropanol | 18% |
| | | Ethyl Acetate | 70% |

Coating was realized by successive immersion of both sides of the capsules into the chosen formulation and suitable drying at room temperature after each immersion. All different types of film-coated capsules have been found to resist in vitro to gastric fluids and to remain buoyant thereupon over a certain period of time. The thus formed capsules were tested one by one utilizing the apparatus here described and schematized in FIG. 1 in which the solvent was 1200 ml HCl pH 1.2 and 0.05% Tween 80 thermostatically maintained at 37.0° C. and wherein the weight transmitter device was assembled with the basket-holder extremity (A) shown in FIG. 3. Readability and sensitivity of recording means were fixed prior essay to standard conditions for floating dosage form measurements (convertion 1 mg=1 mV=0.25 mm, paper speed: 3 cm/hour). The capsules remained positioned lengthways under the mesh basket throughout the entire measuring procedure until they sunk at the moment their bulk density reached the same value as the density of the test solvent. After each essay, the vessel content was withdrawn and replenished by fresh solvent.

Figure 7:
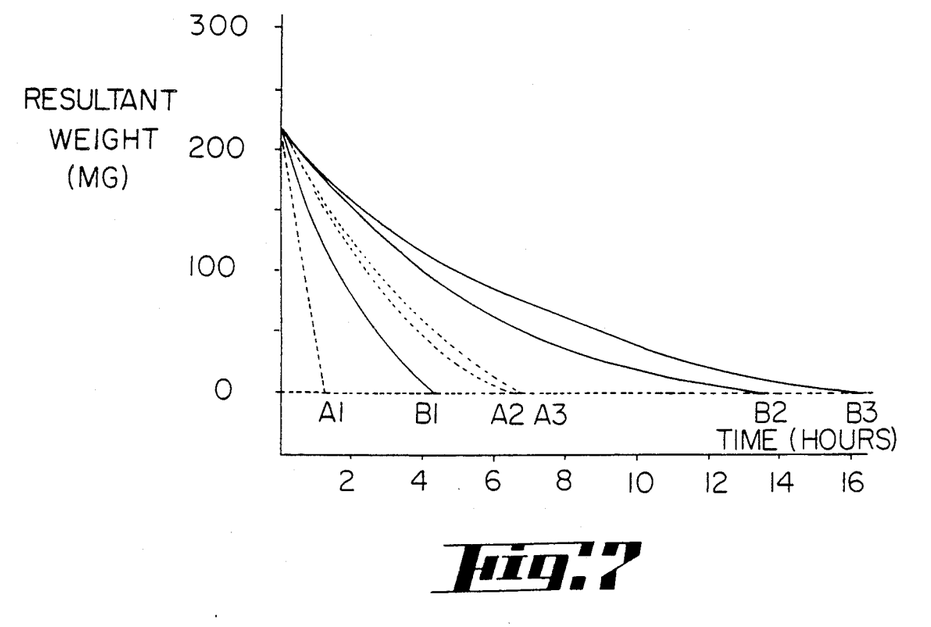
FIG. 7 is a graph illustrating the operation of the apparatus when effecting measurement of the permeability of film-coated capsules described in Example 5.

The comparative resultant-weight mean curves (n=3 for each different type of film-coated capsule) obtained for these tests appear in FIG. 7 with lines A1, A2 and A3 showing respectively the resultant-weight records as a function of time of the capsules having been coated once (A1), twice (A2) or three times (A3) by the film-coating formulation (A), and with the lines B1, B2 and B3 showing respectively the resultant-weight records as a function of time of the capsules having been coated once (B1), twice (B2) or three times (B3) by the film-coating formulation (B). From this data a mean floating duration has been determined for measuring precisely the moment at which the resultant-weight curve is crossing the zero base-line (density=1) and a mean diffusion rate of the solvent through the film has been calculated by counting the weight intake of the capsule until sinking thereof. Mean results are given in Table IV for each different type of film-coated capsule.

TABLE IV

| | Formulation (A) | | | Formulation (B) | | |
|---|---|---|---|---|---|---|
| | A1 | A2 | A3 | B1 | B2 | B3 |
| Floating duration (min.) | 74 | 334 | 400 | 257 | 800 | 963 |
| Diffusion rate (mg/hour) | 178 | 40 | 33 | 51 | 17 | 14 |

It is clearly evident from the above results set forth in FIG. 7 and Table IV that the described apparatus and method are indeed applicable to permability measurements of different film-coating formulations where the aim is to test their resistance to various test solvents. Also, by measuring as a function of time the resultant-weight of an immersed solid material having been coated by a chosen formulation, some important and critical characteristics of the tested coating formulation or about the coating process can be obtained.

The results provided by the invention enable delineation of the gastro-resistance efficacy of the two different coating formulations containing an identical percentage of a gastro-resistant product. In the present context, the invention provides precise information about the behavior of the film coating without necessitating numerous solvent samplings and titrations of a chosen substance mixed into the coated dosage form.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. Apparatus for determining a change in the weight or volume of a test object in an immersed condition as a function of time, said apparatus comprising:
   means for securing a test object partially or totally immersed within a liquid medium;
   means for detecting the magnitude of resultant weight of said test object;
   means connecting said test object securing means and said resultant weight detecting means for transmitting the resultant force acting on said test object from said test object securing means to said resultant weight detecting means, aid test object securing means being characterized by having a waist of relatively small diameter which lies approximately at the surface of the liquid medium when said test object is in an immersed condition;
   whereby changes in the resultant weight of the test object in its immersed condition may be determined by changes in the resultant force acting on the test object.

2. The apparatus of claim 1 wherein said waist ensures a reproducible immersion depth of said test object in its immersed condition in the liquid medium.

3. The apparatus of claim 2 wherein said test object securing means is fabricated of a material which is non-porous, non-absorbing of humidity, solvent-resistant and has an insignificant thermic dilation coefficient.

* * * * *